United States Patent
Louis et al.

(10) Patent No.: US 7,147,664 B2
(45) Date of Patent: Dec. 12, 2006

(54) POSTERIOR VERTEBRAL JOINT PROSTHESIS

(76) Inventors: René Louis, 4 Bis impasse du Roc Fleuri, 13008 Marseille (FR); Patrick Tropiano, 1 rue Martiny, Le Mendoza, 13008 Marseille (FR); Jean-Jacques Bronsard, 10 impasse Vermer, 13007 Marseille (FR); Christian Louis, 122 chemin Carreirade d'Allauch, 13400 Aubagne (FR)

( * ) Notice: Subject to any disclaimer, the term of this patent is extended or adjusted under 35 U.S.C. 154(b) by 0 days.

(21) Appl. No.: 10/493,217

(22) PCT Filed: Nov. 15, 2002

(86) PCT No.: PCT/FR02/03911

§ 371 (c)(1),
(2), (4) Date: May 5, 2004

(87) PCT Pub. No.: WO03/041618

PCT Pub. Date: May 22, 2003

(65) Prior Publication Data

US 2005/0015146 A1 Jan. 20, 2005

(30) Foreign Application Priority Data

Nov. 15, 2001 (FR) .................................. 01 14766

(51) Int. Cl.
*A61F 2/44* (2006.01)

(52) U.S. Cl. .................................................. 623/17.11
(58) Field of Classification Search ... 623/17.11–17.16
See application file for complete search history.

(56) References Cited

U.S. PATENT DOCUMENTS

| | | | | |
|---|---|---|---|---|
| 5,405,400 A | * | 4/1995 | Linscheid et al. | 623/21.15 |
| 5,571,191 A | * | 11/1996 | Fitz | 623/17.11 |
| 6,132,464 A | * | 10/2000 | Martin | 623/17.15 |
| 6,419,703 B1 | * | 7/2002 | Fallin et al. | 623/17.11 |
| 6,565,605 B1 | * | 5/2003 | Goble et al. | 623/17.11 |
| 6,579,319 B1 | * | 6/2003 | Goble et al. | 623/17.11 |
| 6,610,091 B1 | * | 8/2003 | Reiley | 623/17.11 |
| 6,669,729 B1 | * | 12/2003 | Chin | 623/17.11 |
| 6,719,795 B1 | * | 4/2004 | Cornwall et al. | 623/17.11 |
| 6,902,580 B1 | * | 6/2005 | Fallin et al. | 623/17.11 |
| 2002/0065557 A1 | * | 5/2002 | Goble et al. | 623/17.11 |
| 2002/0072800 A1 | * | 6/2002 | Goble et al. | 623/17.11 |

FOREIGN PATENT DOCUMENTS

FR 2721501 12/1995
WO 0130248 5/2001

* cited by examiner

*Primary Examiner*—Eduardo C. Robert
*Assistant Examiner*—Annette Reimers
(74) *Attorney, Agent, or Firm*—Dennison, Schultz & MacDonald

(57) ABSTRACT

A posterior vertebral joint prosthesis is provided so that the left or right posterior vertebral joint prosthesis (1, 2) presents a smooth bearing surface (11, 11a, 11b, 17, 17a, 17b) and and which surface presents antero-posterior curvature.

11 Claims, 3 Drawing Sheets

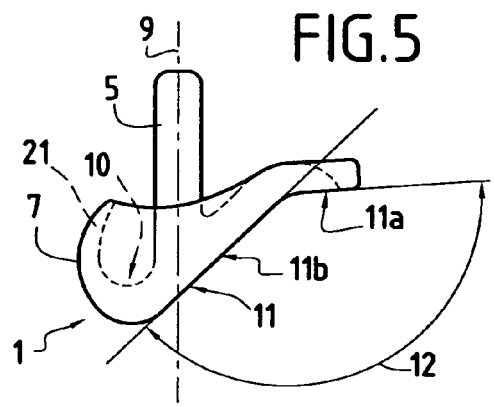
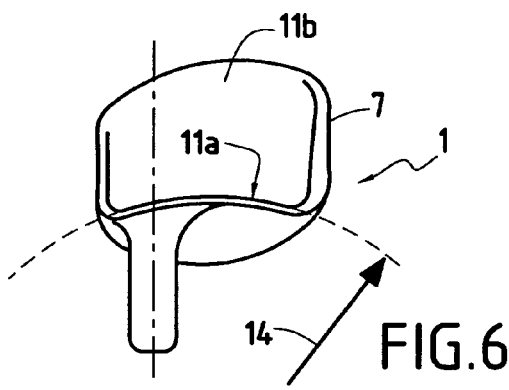
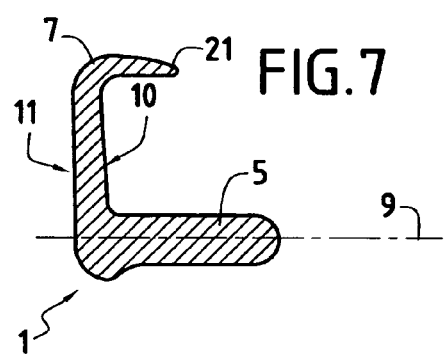
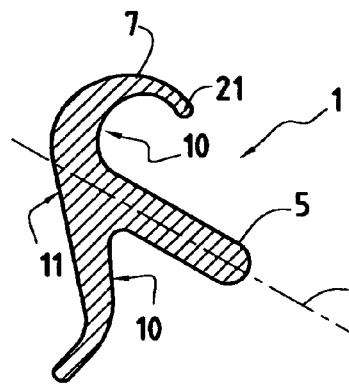
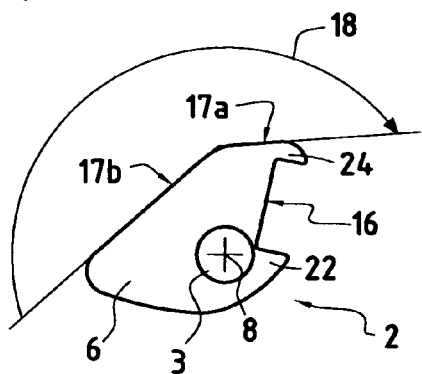
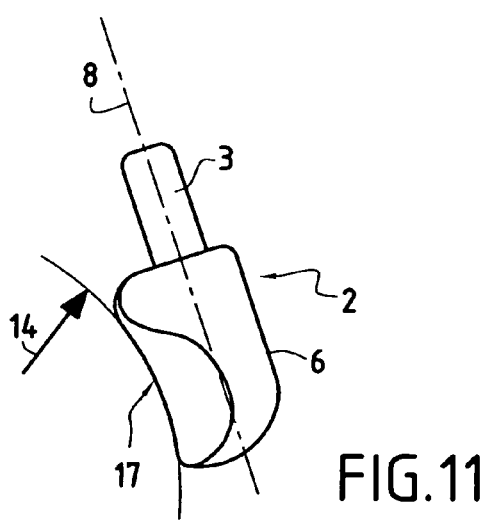
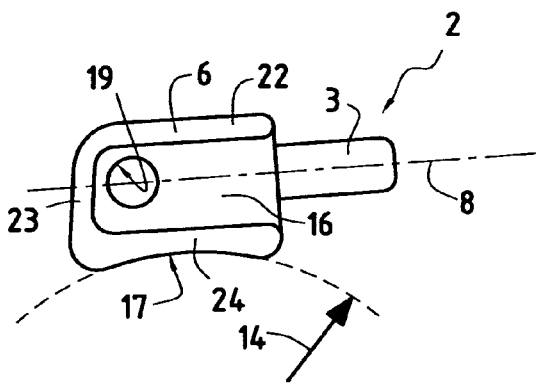

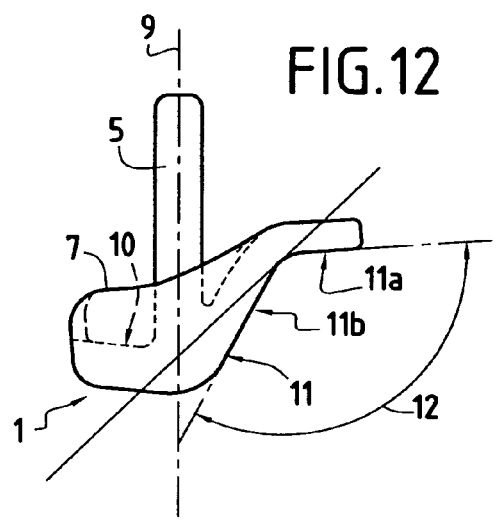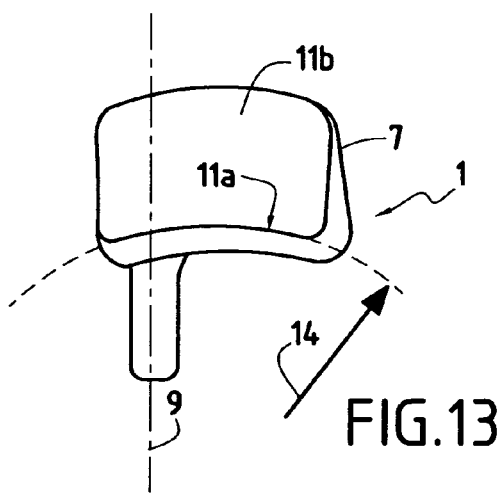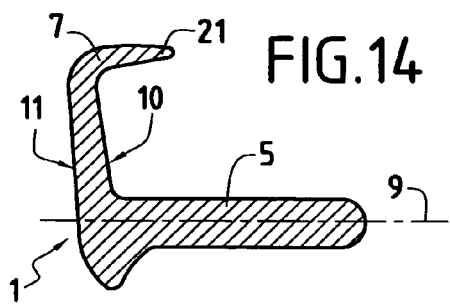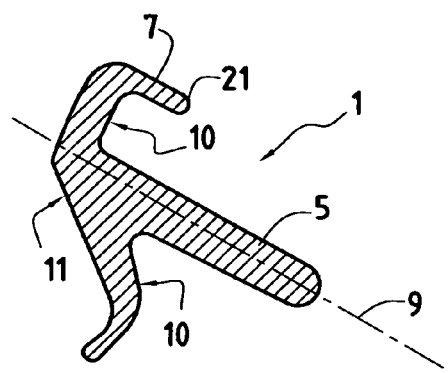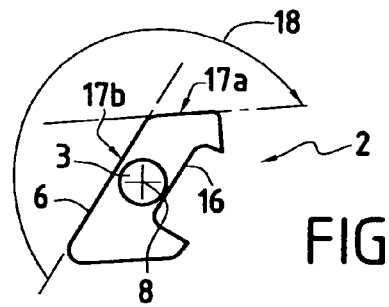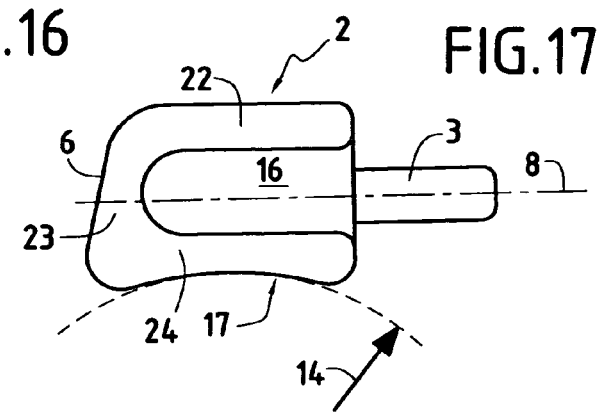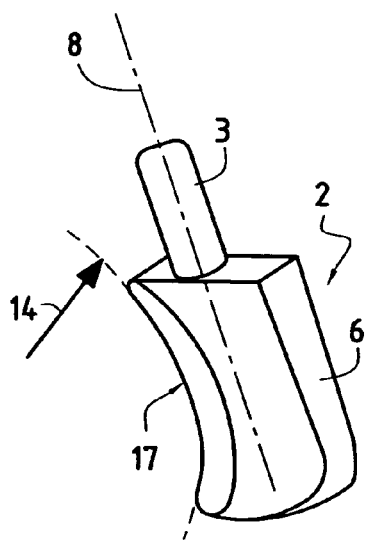

POSTERIOR VERTEBRAL JOINT PROSTHESIS

This application is a 371 of PCT/FR02/03911 filed on Nov. 15, 2002

The present invention relates to a posterior vertebral joint prosthesis.

BACKGROUND OF THE INVENTION

Pain in the cervical, dorsal, and lumbar vertebrae often originates from posterior vertebral joints or zygapophysory joints or "facet" joints. When medical therapy is no longer sufficient for easing the pain, in particular when such joints have become very deformed by arthrosis or old trauma, it becomes desirable to replace their joint surfaces by prostheses; the purpose of such prostheses is to conserve the functions and mobility of the vertebral column, and to avoid the joints becoming blocked (arthrodesis).

Documents FR 2 721 501 and U.S. Pat. No. 6,132,464 describe various devices for replacing the joint surfaces of posterior vertebral facets; each of those devices comprises a support having a convex face fitting closely and coming into bearing contact against a portion of the concave surface of the posterior arc of a vertebra, on at least one side of the spinous process; the support is fixed to the vertebra by a pedicular screw, and/or to the spinous and transverse processes by encircling means such as a band, a collar, or a hook; the device further comprises a strip forming half of a joint prosthesis and having two opposite faces: a first face known as a "joint" or as a "sliding" face which is in contact with a similar face of an adjacent vertebra with minimum friction; said first face being covered in a biocompatible material that slides well, such as stainless steel or titanium, in particular; and a second face opposite from the first face of the strip, known as the "bone" face, which is porous and covered in spikes, is optionally covered in hydroxyapatite, and is intended to bear against the remaining bone of the joint process; the strip is connected to the support by a sessile base whose convex and porous posterior face bears against the bone of the vertebral arch; the means for fixing the support to the spinous and transverse processes and to the pedicle are associated with one another as a function of the anatomic conditions encountered so as to ensure stability for the assembly.

Those devices present certain drawbacks: because of the presence of numerous respective bearing faces on the various portions (support, strip, base) of the device on different regions of a vertebra, it is difficult to ensure that bearing takes place with quality that is uniform and satisfactory because of the variations in shape between one vertebra and another and/or one patient and another; in addition, the presence of the base, the anchoring support, and of the various fixing means contributes to increasing the volume of the prosthesis and consequently to increasing the discomfort for the patient and the trauma due to implanting such a device.

OBJECTS AND SUMMARY OF THE INVENTION

An object of the invention is to propose posterior vertebral joint prostheses that are improved and that remedy the drawbacks of prostheses of this type, at least in part.

In a first aspect, the invention consists in providing a device for a left posterior vertebral joint or for a right posterior vertebral joint, which device comprises a first prosthesis for partially replacing the anterior joint process and that includes a first sliding bearing surface, and a second prosthesis for totally replacing the posterior joint process, including a second sliding bearing surface presenting at least a portion of shape that is similar or identical to the shape of at least a portion of said first sliding bearing surface of said first prosthesis.

Implanting the first prosthesis for partial replacement of the anterior joint process merely requires prior abrasion of the joint surface (or facet) of the anterior process, whereas implanting the second prosthesis for total replacement of the posterior joint process is performed after substantially total ablation of the posterior process.

In another aspect, the invention consists in proposing a device for replacing posterior vertebral joint surfaces, which device comprises, for the left joint and for the right joint, a first prosthesis for the anterior joint process, the first prosthesis including a first smooth bearing surface, and a second prosthesis for the posterior joint process, the second prosthesis including a second smooth bearing surface of a shape that is complementary to the shape of said first surface of the first prosthesis so as to facilitate sliding on the first surface and so as to facilitate relative antero-posterior (or sagittal) pivoting movement between two adjacent vertebrae fitted with these prostheses; this enables two vertebrae fitted with prostheses of the invention to conserve a high degree of mobility.

In another aspect, the invention consists in proposing posterior vertebral joint prostheses presenting smooth sliding bearing surfaces that are substantially V-shaped: the first prosthesis for the anterior joint process including a sliding bearing surface in the form of a concave V-shape with faces preferably forming a first dihedral angle situated in a range 90° to 160°, while the second prosthesis for the posterior joint process includes a sliding bearing surface in the form of a convex V-shape whose faces form a second dihedral angle of value equal to or close to the 360° complement of the value of said first dihedral angle.

Putting said first and second prostheses into mutual contact via their respective smooth V-shaped bearing surfaces encourages mutual guidance of these two prostheses during their mutual sliding displacement, thereby increasing the dynamic stability of a spine in which two adjacent vertebrae are fitted with such prostheses.

The magnitude of the open dihedral angle of the V-shaped sliding bearing surfaces is preferably adapted to the position of the vertebra along the spine: for the lumbar-sacral L5-S1 joint, the magnitude of the angle of the anterior joint prosthesis is preferably close to 90° to 160° and the magnitude of the angle of the posterior joint prosthesis is respectively close to 270° to 200°, whereas for the L4-L5 joint, the angle of the anterior prosthesis is preferably close to 90° to 150°, and the angle of the posterior prosthesis is respectively close to 270° to 210°.

In another aspect, the invention consists in providing posterior vertebral joint prostheses presenting smooth sliding bearing surfaces presenting antero-posterior curvature: said anterior first prosthesis presents (in medial view) a rearwardly-open curved sliding surface, and said posterior second prosthesis presents (in medial view) a forwardly-closed curved sliding surface of curvature equal to (or close to) the curvature of the open surface of the first prosthesis; this facilitates free relative antero-posterior pivoting of two adjacent vertebrae fitted with these prostheses; the antero-posterior radius of curvature of these sliding surfaces can be adapted to the position of the vertebra for which the prosthesis is intended; the magnitude of this radius is preferably selected from a range of 18 millimeters (mm) to 28 mm, more preferably 20 mm to 26 mm, and in particular close to 23 mm.

By means of this curvature, flexion-extension movements of the vertebral column (antero-posterior pivoting) can be performed about a common transverse axis for the intervertebral disk and for the joints.

In a preferred embodiment, the sliding surfaces present both a V-shape and antero-posterior (sagittal) curvature: the anterior prosthesis has a sliding surface in the form of a concave V-shape comprising a rearwardly-convex medial face with a radius of curvature close to 20 mm to 26 mm, and a substantially plane lateral face; the posterior prosthesis has a sliding surface in the form of a convex V-shape comprising a forwardly-concave medial face with a radius of curvature close to 20 mm to 26 mm, and a substantially plane lateral face; in other words, in this case, said sliding surfaces extend substantially along a surface of revolution generated by a curved segment turning about a (transverse) straight line situated in a plane containing the curved segment, and at a distance therefrom which is equal to said radius of curvature; as a result, the sliding surfaces of the left and right prostheses are substantially in the shape of portions of a kind of circularly toroidal groove.

In another aspect, the invention consists in providing an anterior prosthesis for a posterior vertebral joint, the prosthesis comprising a smooth sliding bearing surface and a bone bearing surface, together with an anchor structure for anchoring the prosthesis in the joint process and projecting from said bone bearing surface; the invention also provides a posterior prosthesis for a posterior vertebral joint, the prosthesis comprising a sliding bearing surface and a bone bearing surface, together with an anchor structure for anchoring the prosthesis in the vertebral isthmus and/or in the vertebral lamina, which structure projects from said bone bearing face.

The invention makes it possible to obtain prostheses that are well adapted to human anatomy, that are compact, stable, and not very traumatizing.

Preferably, each of the anchor structures comprises an elongate anchor member—such as a stud or a rod—extending along an axis which is generally inclined relative to the normal to the bone bearing surface; said anchor member is preferably substantially cylindrical in shape about said axis, and is threaded or provided with grooves or projections on its outer face in order to increase bone contact area.

Specifically, for an anterior prosthesis, the anchoring that results from this member can be improved by the presence of a rib projecting along a portion of the periphery of the bone bearing surface, thereby increasing contact area with the bone.

Specifically, for a posterior prosthesis, anchoring can be improved by the presence of two elongate anchor members—such as rods or studs—extending along two substantially orthogonal axes.

Said elongate anchor members may form a single part together with the prosthesis body that includes the bone bearing face and the sliding bearing face; alternatively, or in addition, a distinct anchor member may be used, in particular in the form of a screw passing through an orifice provided in the prosthesis body.

BRIEF DESCRIPTION OF THE DRAWINGS

Other advantages and characteristics of the invention will be understood on reading the following description which refers to the accompanying drawings which show preferred embodiments of the invention that are of no limiting character.

FIGS. 5 to 8 show an embodiment of an anterior joint prosthesis adapted to the lumbar-sacral joint L5-S1, and FIGS. 9 to 11 show a posterior joint prosthesis complementary to the prosthesis of FIGS. 5 to 8.

Like FIGS. 5 to 8, FIGS. 12 to 15 show embodiments of an anterior joint prosthesis adapted for the posterior joint between lumbar vertebrae L4 and L5, and FIGS. 16 to 18 show a posterior joint prosthesis complementary to the prosthesis of FIGS. 12 to 15.

FIGS. 5, 9, 12, and 16 are cranial views of the prostheses;

FIGS. 6, 10, 13, and 17 are medial views of the prostheses;

FIGS. 17 and 14 are sagittal views;

FIGS. 8 and 15 are horizontal views; and

FIGS. 11 and 18 are lateral views.

FIGS. 7, 8, 14, and 15 are section views.

MORE DETAILED DESCRIPTION

Although the invention is described below in association with the lumbar portion of the spine, the invention is applicable to the posterior joints of dorsal and cervical vertebrae as well.

Figure 1:
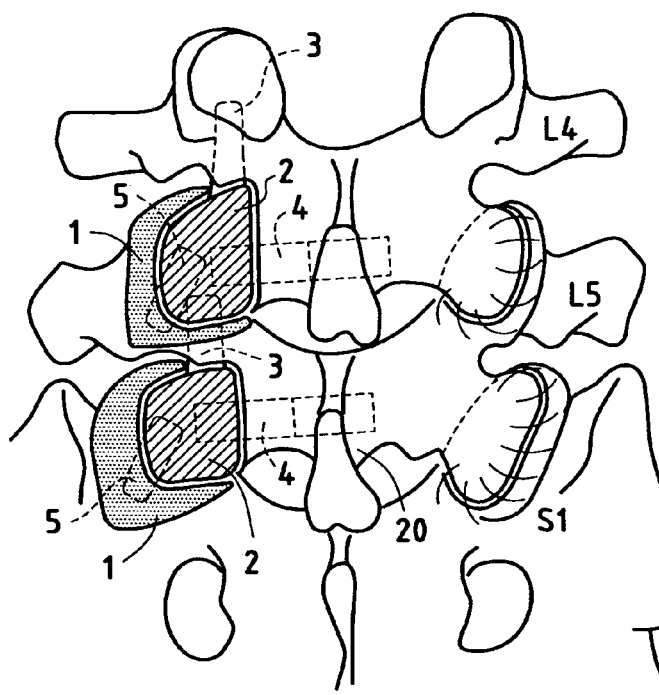
FIG. 1 is a diagrammatic dorsal view of the top portion of the sacrum and of lumbar vertebrae L4 and L5, with four left posterior joint prostheses being shown thereon replacing two superposed left posterior joints.
Figure 2:
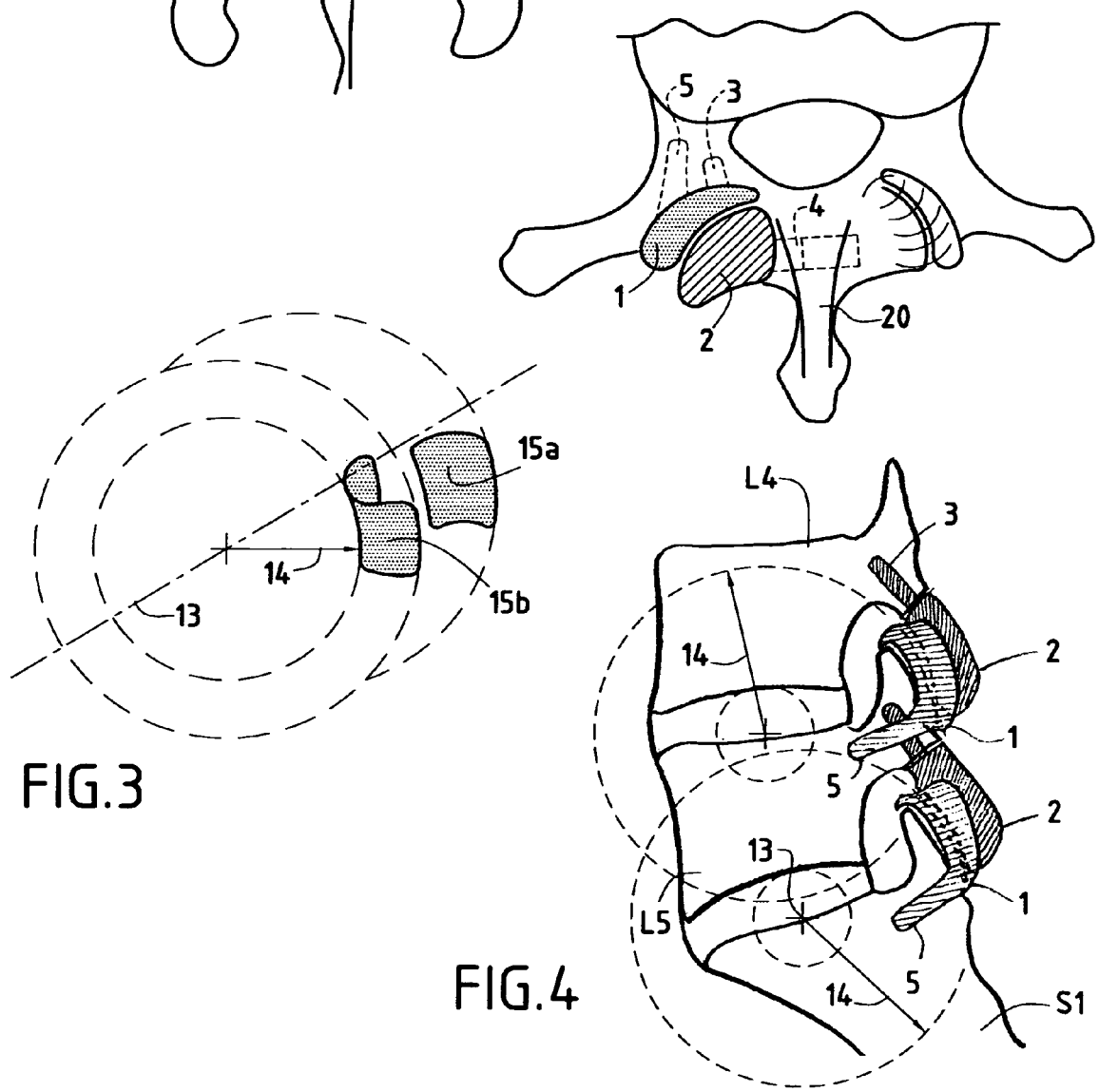
FIG. 2 is a diagram in cranial view of a left anterior joint prosthesis and a left posterior joint prosthesis replacing a posterior joint between two successive vertebrae of the spine.
Figure 3:
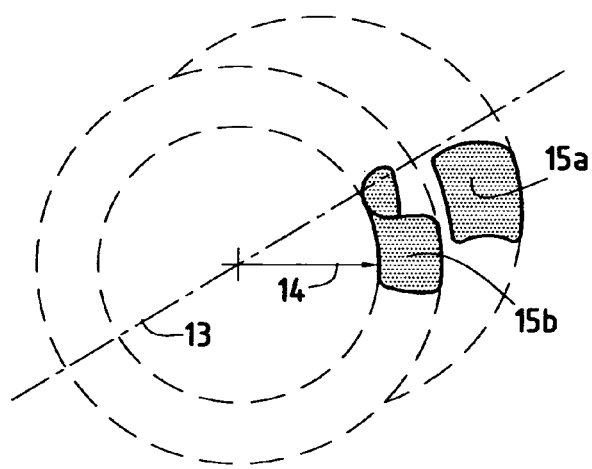
FIG. 3 is a diagrammatic perspective view showing the shape of the sliding bearing surfaces of prostheses of the invention.
Figure 4:
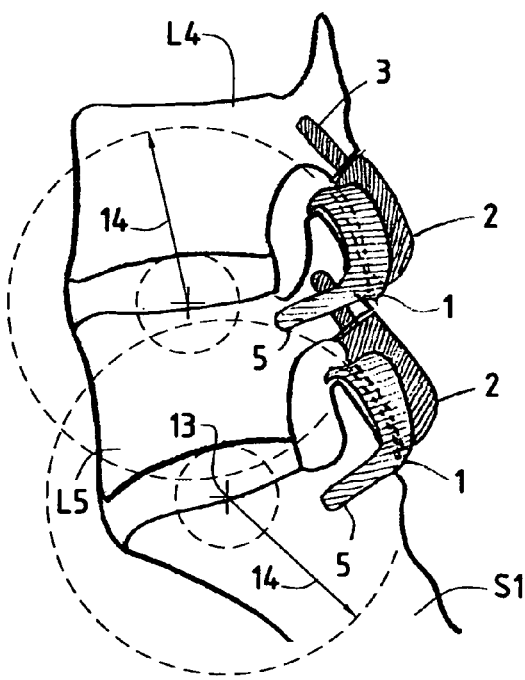
FIG. 4 is a diagrammatic side view of vertebrae fitted with joint prostheses and how they move in mutual pivoting about a transverse axis.

With reference to FIGS. 1 and 2 in particular, a left or right posterior vertebral joint is replaced by using an anterior prosthesis 1 referred to as a "first" prosthesis, and a posterior prosthesis 2 referred to as a "second" prosthesis. The anterior prosthesis 1 is fixed on a vertebra such as L5 or to the sacrum S1, while the posterior prosthesis 2 is fixed to the vertebra situated immediately thereabove, such as L4 or L5, respectively.

With reference to FIGS. 5 to 18 in particular, each of the prostheses 1 and 2 comprises a body 6, 7 and a cylindrical anchor rod 3, 5 integrated in the body and elongate along an axis 8, 9.

With reference to FIGS. 5 to 8 and 12 to 15, the body 7 of the anterior prosthesis 1 is defined to a large extent by two opposite surfaces: a surface 10 enabling the prosthesis to bear against the stump of the anterior joint process, and a surface 11 for sliding contact with the posterior prosthesis (reference 2); as shown in particular in the cranial views (FIGS. 5 and 12), the surface 11 has two faces 11a and 11b forming a kind of V-shape with a rearwardly-open dihedral angle 12 of about 140° for the L5-S1 prosthesis of FIG. 5 and close to 120° for the L4-L5 prosthesis of FIG. 12; in addition, these faces 11a, 11b extend along an intermediate surface 15a, 15b which is circularly cylindrical about a transverse axis 13 having a radius of curvature 14 (see FIGS.

3 and 4) that is close to 23 mm; the medial portion 11a of the sliding surface 11 is convex, while the lateral portion 11b of the surface 11 is plane.

In complementary manner, each posterior prosthesis 2, FIGS. 9 to 11 and 16 to 18, presents a surface 16 for bearing against the bone and a surface 17 for bearing in sliding manner on the surface 11 of the corresponding prosthesis 1; the surface 17 comprises a face 17a and a face 17b that form a convex V-shape (FIGS. 9 and 16) with an open dihedral angle 18 of about 220° (FIG. 9) or about 240° (FIG. 16); the medial portion 17a of the sliding surface 17 is concave while the lateral portion 17b is substantially plane.

The concave side of the V-shape 11a, 11b of the anterior prosthesis faces rearwards, whereas the convex side of the V-shape 17a, 17b of the posterior prosthesis faces forwards.

The L5-S1 posterior prosthesis (FIG. 10) includes an orifice 19 specially designed to receive an additional anchor screw (referenced 4, FIGS. 1 and 2) for anchoring the prosthesis in the lamina 20 of the vertebral arch.

Retention of the prostheses 1 and 2 is reinforced by the presence of stabilizing ribs 21 (see FIGS. 5, 7, and 8, in particular), 22, 23, and 24 (see FIGS. 10 and 17) which project from the periphery of the bone-bearing surface 10, 16; with the posterior prosthesis 2, the ribs 22 to 24 and the surface 16 define a groove or gully.

Preparation for implanting the prostheses requires a posterior approach exposing the posterior joint(s) to be replaced. At least partial excision (ablation) of the joint processes is necessary. On the anterior facet (or joint process) (or on the superior joint process of the underlying vertebra) the joint surface is merely abraded so as to reduce the total volume of the facet and provide a sagittal anchor hole in its lower portion. On the posterior facet (or joint process) (or on the lower joint process of the underlying vertebra) sub-total ablation is performed with oblique section towards the vertebral lamina and perpendicular section over the vertebral isthmus, and two anchor holes, a sagittal hole on the axis of the isthmus towards the vertebral pedicle, and a transverse hole in the thickness of the vertebral lamina are hollowed out from the spinal process.

The anterior prosthesis 1 bears against the prepared stump of-the-anterior facet with its cylindrical anchoring stud penetrating in the anchor hole. The prosthesis presents a smooth joint surface 11, 11a, 11b on its rearwardly-facing face of a shape that presents a rearwardly-open V-shaped section (or a section like a pulley wheel groove), with a narrow front medial sector and a broad and oblique lateral sector. In horizontal section, the medial sector is a frontal sector and the lateral sector presents obliqueness lying in the range 50° to 20° going from the sacrum to the top of the lumbar column. In sagittal section, the medial and lateral sectors 11a and 11b of the prosthesis have rearwardly-directed convex sides corresponding to the arc of a circle whose center corresponds to the common pivot center between the two posterior joints and the intervertebral disk for a given moving segment of the spine (the radius of this circle is 23 mm on average).

The posterior prosthesis 2 presents a first integral stud 3 provided for engaging in the anchor hole in the isthmus, and a second stud 4 which is separate from the body of the prosthesis and which is screwed for anchoring to the lamina. The forwardly-directed sliding joint surface 17, 17a, 17b bears intimately against the joint surface 11, 11a, 11b of the anterior prosthesis 1.

The prostheses 1 and 2 may be made of metal or of plastics material or of any other material that is biologically compatible. The retention of the prostheses can be reinforced by means of plastic cement.

What is claimed is:

1. A left or right posterior vertebral joint prosthesis presenting a smooth sliding bearing surface, wherein said sliding bearing surface has a medial face and a plane lateral face, said medial face and said lateral face forming a rearwardly-open dihedral angle and said medial face having a radius of curvature lying in the range of 18 mm to 28 mm so as to facilitate sagittal pivoting of two adjacent vertebrae fitted with such joint prosthesis around a common transverse axis between two posterior joints and the intervertebral disk for a given moving segment of the spine, said surface being suitable for co-operating with a complementary bearing surface of a complementary joint prosthesis fitted on an adjacent vertebrae.

2. A prosthesis according to claim 1, further comprising a bone bearing surface and an anchor structure, and in which the anchor structure projects from the bone bearing surface.

3. A prosthesis according to claim 2, in which at least a portion of the anchor structure is integral with the body of the prosthesis.

4. A prosthesis, according to claim 2, in which the anchor structure includes an anchor member that is elongate along an axis that is inclined relative to the normal of the bone bearing surface.

5. A prosthesis according to claim 4, in which the anchor member is substantially cylindrical in shape.

6. A prosthesis according to claim 4, in which said anchor member is provided on its outside surface with grooves or projections.

7. A prosthesis according to claim 1, for replacing the anterior joint process, in which at least a portion of said medial face is convex, rearwardly open, and curved with a radius lying in the range 18 mm to 28 mm.

8. A prosthesis according to claim 7, for replacing the anterior joint process, in which said dihedral angle is lying in the range of 90 to 160.

9. A prosthesis according to claim 1, for replacing the posterior joint process, in which at least a portion of said smooth bearing surface is concave, forwardly closed, and curved with a radius lying in the range 18 mm to 28 mm.

10. A prosthesis according to claim 9, for replacing the posterior joint process, in which said dihedral angle is lying in the range 200 to 270.

11. A device for replacing a left or right posterior vertebral joint, the device comprising:
    a prosthesis for partially replacing the anterior joint process, referred to as the "first" prosthesis, which prosthesis is in accordance with claim 1, and has a first smooth sliding bearing surface in the form of a section of a pulley groove; and
    a prosthesis for replacing the posterior joint process, referred to as the "second" prosthesis, which is in accordance with claim 1, and which includes a second smooth sliding bearing surface, of which at least a portion is similar or complementary in shape to at least a portion of said first smooth sliding bearing surface of said first prosthesis, so as to facilitate relative sagittal pivoting movement between two adjacent vertebrae fitted with these prostheses.

* * * * *